(12) United States Patent
Chen et al.

(10) Patent No.: US 9,610,268 B2
(45) Date of Patent: Apr. 4, 2017

(54) TRANS-ACONITIC ACID COMPOUNDS AND USES THEREOF FOR INHIBITING PHOSPHODIESTERASE 7

(71) Applicant: Academia Sinica, Taipei (TW)

(72) Inventors: Shui-Tein Chen, Taipei (TW); I-Shu Lee, Zhuangwei Township, Yilan County (TW); Yu-Chun Chen, Taipei (TW)

(73) Assignee: Academia Sinica, Taipei (TW)

( * ) Notice: Subject to any disclaimer, the term of this patent is extended or adjusted under 35 U.S.C. 154(b) by 219 days.

(21) Appl. No.: 14/513,029

(22) Filed: Oct. 13, 2014

(65) Prior Publication Data

US 2015/0104531 A1  Apr. 16, 2015

Related U.S. Application Data

(60) Provisional application No. 61/889,778, filed on Oct. 11, 2013.

(51) Int. Cl.
| | | |
|---|---|---|
| *A61K 36/00* | (2006.01) | |
| *A61K 31/194* | (2006.01) | |
| *A61K 36/9062* | (2006.01) | |
| *A61K 36/899* | (2006.01) | |
| *A61K 36/8998* | (2006.01) | |

(52) U.S. Cl.
CPC .......... *A61K 31/194* (2013.01); *A61K 36/899* (2013.01); *A61K 36/8998* (2013.01); *A61K 36/9062* (2013.01)

(58) Field of Classification Search
None
See application file for complete search history.

(56) References Cited

U.S. PATENT DOCUMENTS

2008/0089957 A1*  4/2008  Chen ................. A61K 36/45
                                                          424/725
2009/0298945 A1* 12/2009  Chen ................. A61K 31/194
                                                          514/574

OTHER PUBLICATIONS

De Faria Garcia et al, Antiedematogenic activity and phytochemical composition of preparations from Echinodorus grandiflorus leaves. Phytomedicine (2011), vol. 18, No. 1, pp. 80-86.*

* cited by examiner

*Primary Examiner* — Qiuwen Mi
(74) *Attorney, Agent, or Firm* — Muncy, Geissler, Olds & Lowe, P.C.

(57) ABSTRACT

Methods of inhibiting a phosphodiesterase (PDE) 7 enzyme such as PDE7A1 and methods for treating diseases associated with PDE7 using one or more trans-aconitic acid compounds, which can be isolated from plants.

10 Claims, 3 Drawing Sheets

TRANS-ACONITIC ACID COMPOUNDS AND USES THEREOF FOR INHIBITING PHOSPHODIESTERASE 7

CROSS-REFERENCE TO RELATED APPLICATION

This application claims priority to U.S. provisional application No. 61/889,778, filed Oct. 11, 2013, the entireties of which is incorporated herein by reference.

BACKGROUND OF THE INVENTION

1. Field of the Invention

The present disclosure relates to a method of inhibiting phosphodiesterase 7. More particularly, the disclosed invention relates to the use of an aconitic acid for inhibiting phosphodiesterase 7.

2. Description of Related Art

Aconitic acid is an organic acid having two isomers, cis-aconitic acid and trans-aconitic acid. Cis-aconitic acid is an intermediate of the citric acid cycle. Trans-aconitic acid is a defense metabolite in plant.

Phosphodiesterases (PDE) are a superfamily of enzymes that break a phosphodiester bond. The superfamily of PDE enzymes is classified into 11 families, PDE1-PDE11. While different PDEs are functionally related, their amino acid sequences can show considerable divergence. Different PDEs also have different substrate specificities. For example, PDE4, 7 and 8 are cAMP-selective hydrolases; PDE 5, 6, and 9 are cGMP-selective hydrolases, and PDE1, 2, 3, 10, and 11 can hydrolyze both cAMP and cGMP. Phosphodiesterase enzymes are often targets for treating various diseases and disorders due to their unique tissue distribution, structural properties, and functional properties.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

The present disclosure is based on the unexpected discovery that trans-aconitic acid (TAA) specifically inhibits PDE7, particularly PDE7A1.

Accordingly, one aspect of the present disclosure features a method for inhibiting a phosphodiesterase 7 (PDE7), comprising: contacting a PDE7 with a composition comprising a trans-aconitic acid compound (e.g., TAA) in an amount effective in inhibiting the activity of the PDE7. In some examples, the PDE7 (e.g., PDE7A1) is a human enzyme.

In some embodiments, the composition used in any of the methods described herein is a plant extract, which may be prepared from a monocotyledon plant, e.g., shell flower, rice, wheat grass, maize, barley, or sorghum. In one example, the plant extract is prepared from leaves or straws of the plant, such as leaves or straws of rice, leaves of shell flower, or wheat grasses.

In other embodiments, the composition used in any of the methods described herein comprises the trans-aconitic compound that is purified from a plant, e.g., a monocotyledon plant such as shell flower, rice, wheat grass, maize, barley, or sorghum.

In yet other embodiments, the composition used in any of the methods described herein comprises the trans-aconitic acid compound that is chemically synthesized.

In any of the methods described herein, the contacting step can be performed by administering the composition that comprises the trans-aconitic acid compound to a subject in need thereof, wherein the composition is a pharmaceutical composition which further comprises a pharmaceutically acceptable carrier. In some embodiments, the subject (e.g., a human patient) has or is at risk for a disease associated with dysregulation of the PDE7, which can be an inflammatory disease (e.g., rheumatoid arthritis, eczema, atopic dermatitis, and allergic rhinitis), an autoimmune disease, a cardiovascular disease, a neurodegenerative disease, and cancer.

Also within the scope of the present disclosure are (a) pharmaceutical compositions for use in treating a disease a disease associated with dysregulation of the PDE7, which can be an inflammatory disease (e.g., rheumatoid arthritis, eczema, atopic dermatitis, and allergic rhinitis), an autoimmune disease, a cardiovascular disease, a neurodegenerative disease, and cancer, wherein the pharmaceutical composition comprises a trans-aconitic acid compound (e.g., TAA) and a pharmaceutically acceptable carrier; and (b) use of a trans-aconitic acid compound for manufacturing a medicament for use in treating a disease associated with dysregulation of PDE7 such as those described herein.

The details of one or more embodiments of the invention are set forth in the description below. Other features or advantages of the present invention will be apparent from the following drawing and detailed description of several embodiments, and also from the appended claims.

BRIEF DESCRIPTION OF THE DRAWINGS

The present description will be better understood from the following detailed description read in light of the accompanying drawings, where.

DESCRIPTION

Figure 1:
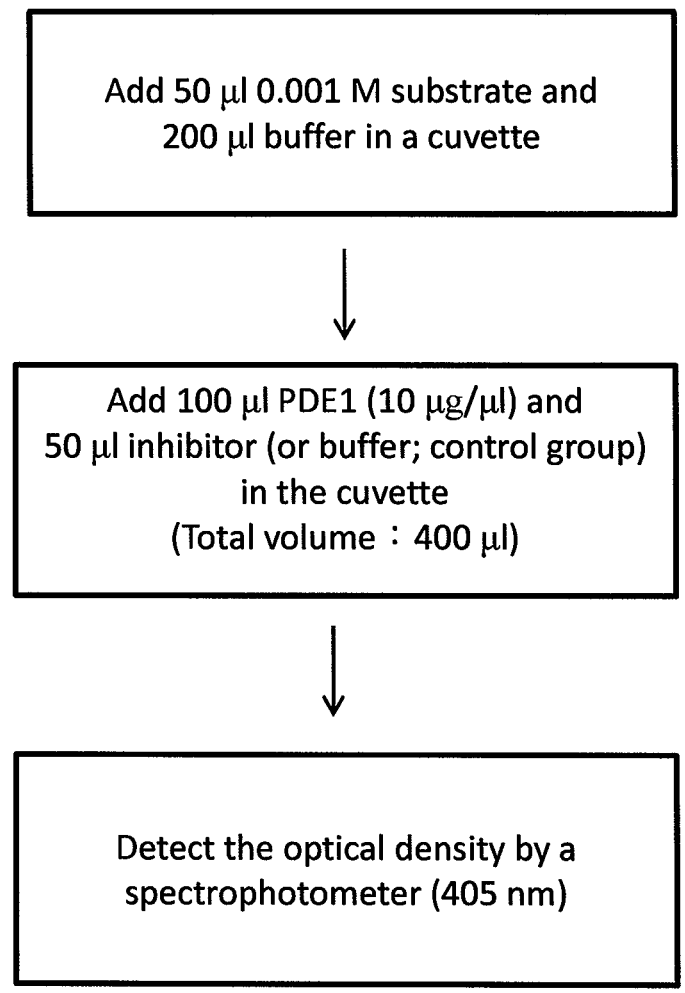
FIG. 1 is a diagram showing an assay for determining PDE1 enzymatic activity.

The present disclosure is based on the unexpected discovery that TAA, which can be purified from plants such as rice, shell flower, or wheat grass, specifically inhibits PDE7 such as PDE7A1, but not PDE1. Thus, this compound, as well as its functional analogs, can be used in treating diseases associated with dysregulation of PDE7 (e.g., PDE7A1) and avoiding side effects caused by inhibiting other PDE family members, such as PDE1.

Accordingly, described here are methods for inhibiting the activity of PDE7 comprising contacting PDE7 with an effective amount of one or more TAA compounds and methods for treating a disease associated with PDE7 comprising administering to a subject in need of the treatment a pharmaceutical composition comprising an effective amount of one or more TAA compounds.

I. Trans-Aconitic Acid (TAA) Compounds and Compositions Comprising Such

Trans-aconitic acid compounds include trans-aconitic acid (TAA) and its functional analogs. TAA has the structure shown below:

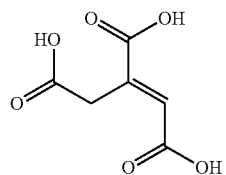 [SMILES: O=C(O)/C=C(\CC(=O)O)C(=O)O]

A functional analog of TAA can have a structure substantially similar to TAA and a substantially similar bioactivity as TAA (e.g., specifically inhibits PDE7A). A compound that specifically inhibits PDE7 (e.g., PDE7A1) is a compound that exhibits an inhibitory activity against the PDE7 enzyme substantially greater than its inhibitory activity against another PDE enzyme. For example, the inhibitory activity of the compound against the PDE7 enzyme can be at least 50% higher (e.g., at least 75%, 80%, 90%, 1-fold, 5-fold, 10-fold, 50-fold, 100-fold, or 1000-fold higher) than its inhibitory activity against the other PDE enzyme (e.g., PDE1). In some instances, the TAA compound that specifically inhibits PDE7 shows no inhibitory activity against another PDE enzyme (e.g., PDE1) in a routine assay for determining the enzymatic activity of the PDE enzyme.

In some examples, a functional analog of TAA can be a substituted TAA, in which one or more hydrogen atoms are replaced with a substituent. Examples of substituents include, but are not limited to, halogen, cyano, nitro, hydroxyl, amino, mercapto, alkyl, alkenyl, alkynyl, aryl, heteroaryl, cyclyl, heterocyclyl, alkyloxy, aryloxy, alksulfanyl, arylsulfanyl, alkylamino, arylamino, dialkylamino, diarylamino, alkylcarbonyl, arylcarbonyl, heteroarylcarbonyl, alkylcarboxyl, arylcarboxyl, heteroarylcarboxyl, alkyloxycarbonyl, aryloxycarbonyl, heteroaryloxycarbonyl, alkylcarbamido, arylcarbamido, heterocarbamido, alkylcarbamyl, arylcarbamyl, heterocarbamyl, wherein each of alkyl (including alk), alkenyl, aryl, heteroaryl, cyclyl, and heterocyclyl is optionally substituted with halogen, cyano, nitro, hydroxyl, amino, mercapto, alkyl, aryl, heteroaryl, alkyloxy, aryloxy, alkylcarbonyl, arylcarbonyl, alkylcarboxyl, arylcarboxyl, alkyloxycarbonyl, or aryloxycarbonyl.

TAA compounds as described herein can be synthesized by conventional methods. For example, one can use synthetic chemistry transformations (including protecting group methodologies), e.g., those described in R. Larock, *Comprehensive Organic Transformations*, VCH Publishers (1989); T. W. Greene and P. G. M. Wuts, *Protective Groups in Organic Synthesis,* 3rd Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

Alternatively, the TAA compounds as described herein can be purified from a natural source, such as plants (e.g., a monocotyledon plant such as shell flower, shell flower, rice, wheat grass, maize, barley, or sorghum) following routine technology, for example, the method described in Example 1. A TAA compound purified from a natural source such as a plant refers to a TAA compound (e.g., TAA) that is substantially free from naturally associated molecules, i.e., the naturally associated molecules constituting at most 20% by dry weight of a preparation containing the TAA compound. Purity can be measured by any appropriate method, e.g., column chromatography, polyacrylamide gel electrophoresis, and HPLC. In some embodiments, a TAA compound can be purified from a plant by soaking a part of the plant (e.g., leaf, root, seed, flower, or tuber) in a suitable amount of pure water or a water-containing solvent for a suitable period of time (e.g., 5 minutes to an hour) at a suitable temperature (e.g., 60° C. to 90° C.) and then collecting the water-soluble fraction thus formed. Chromatography or other methods known in the art can be applied to further purify the TAA compound from the water-soluble fraction.

Any of the TAA compounds described herein can be mixed with a pharmaceutically acceptable carrier to form a pharmaceutical composition.

A pharmaceutically acceptable carrier is a carrier compatible with the active ingredient of the composition (and preferably, capable of stabilizing the active ingredient) and not deleterious to the subject to be treated. Suitable carriers include, but are not limited to, (a) salts formed with cations (e.g., sodium, potassium, ammonium, magnesium, calcium) and polyamines (e.g., spermine and spermidine); (b) acid addition salts formed with inorganic acids (e.g., hydrochloric acid, hydrobromic acid, sulfuric acid, phosphoric acid, nitric acid); (c) salts formed with organic acids (e.g., acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid); and (d) salts formed from elemental anions (e.g., chlorine, bromine, and iodine). Other suitable carriers include microcrystalline cellulose, mannitol, glucose, defatted milk powder, polyvinylpyrrolidone, starch, and a combination thereof. See, e.g., Remington's Pharmaceutical Sciences, Edition 18, Mack Publishing Co., Easton, Pa. (1995); and Goodman and Gilman's "The Pharmacological Basis of Therapeutics", Tenth Edition, Gilman, J. Hardman and L. Limbird, eds., McGraw-Hill Press, 155-173, 2001. One or more solubilizing agents can be utilized as pharmaceutical excipients for delivery of the TAA-containing composition. Examples of other carriers include colloidal silicon oxide, magnesium stearate, cellulose, sodium lauryl sulfate, and D&C Yellow #10.

The composition comprising one or more TAA compounds as described herein can be formulated in forms suitable for various routes of administrations.

A sterile injectable composition can be a solution or suspension in a non-toxic parenterally acceptable diluent or solvent, such as a solution in 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or diglycerides). Fatty acid, such as oleic acid and its glyceride derivatives are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art.

A composition comprising one or more TAA compounds can also be administered in the form of suppositories for rectal administration.

In some embodiments, the composition comprising one or more TAA compounds can be a water extract prepared from a monocotyledon plant, i.e., a plant having one cotyledon, or embryonic leaf, in its seeds. Examples of monocotyledon plants suitable for preparing the TAA-containing compositions described herein include, but are not limited to, rice, shell flower, maize, wheat grass, barley, or sorghum. Preferably, the monocotyledon plant is a crop, which refers to a plant grown in significant quantities to be harvested as food, livestock fodder, or any other economic purposes. A water extract of a plant can be prepared by soaking a part of the plant (e.g., leaf, root, seed, flower, or tuber) in a suitable amount of pure water or a water-containing solvent for a suitable period of time (e.g., 5 minutes to an hour) at a suitable temperature (e.g., 60° C. to 90° C.) and then collecting the water-soluble fraction thus formed, which can be dried by, e.g., spray drying or freeze-drying, subsequently to obtain a water extract in powder form. Chromatography or other methods known in the art can be applied to confirm the existence of TAA in the water extract thus prepared. Cardioprotection effects, such as relaxation of vascular contraction and lowering blood pressure, can be determined by both in vivo and in vitro studies as described herein or known in the art.

In other embodiments, the composition comprising one or more TAA compounds are formulated as food supplements, which may further comprises additional nutritional components, such as vitamins, minerals, fiber, fatty acids, or amino acids.

II. Uses of TAA Compounds for Inhibiting PDE7 and Treating Diseases Associated with PDE7

Any of the TAA compounds or compositions comprising such can be used to specifically inhibit the activity of PDE7 such as PDE7A1 and for treating diseases associated with the dysregulation of the enzyme. Thus, described herein are methods for inhibiting a PDE7 enzyme comprising contacting the enzyme with one or more of the TAA compounds or compositions comprising such and methods for treating diseases associated with the enzyme comprising administering to a subject in need of the treatment an effective amount of one or more TAA compounds or compositions comprising such.

PDE7 is a member of the PDE family. There are two isoforms of PDE7, i.e., PDE7A and PDE7B. PDE7A is a high affinity cAMP-specific PDE that is expressed abundantly in heart, skeletal muscles and spleen. PDE7A1, a splice variant of PDEA, is mainly expressed in lymphocytes and pro-inflammatory cells. PDE7B is mainly expressed in central nervous system, especially in caudate nucleus and nucleus accumbens. PDE7B1 can be activated by D1 agonist in striatal neurons, suggesting that PDE7B1 may play a role in memory. Since PDE7 is associated with various diseases, such as neurological or inflammatory disorders, it is of great interest to identify new PDE7 inhibitors for treating such disorders.

The term "treating" as used herein refers to the application or administration of a composition including one or more active agents to a subject, who has a disease associated with dysregulation of a PDE7 enzyme, a symptom of the disease, or a predisposition toward the disease, with the purpose to cure, heal, alleviate, relieve, alter, remedy, ameliorate, improve, or affect the disease, the symptoms of the disease, or the predisposition toward the disease.

To practice the methods described herein, an effective amount of a composition comprising one or more of TAA compounds, e.g., a pharmaceutical composition, a plant extract, or a food supplement as described herein, can be administered to a subject via a conventional route, e.g., parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique.

"An effective amount" as used herein refers to the amount of each active agent required to confer therapeutic effect on the subject, either alone or in combination with one or more other active agents. Effective amounts vary, as recognized by those skilled in the art, depending on route of administration, excipient usage, and co-usage with other active agents.

The compositions comprising TAA compounds as described herein are administered in effective amounts. An "effective amount" is that amount of a TAA-containing composition that alone, or together with further doses, produces the desired response, e.g. inhibiting the activity of a PDE7 enzyme such as PDE7A1 or alleviating a disease associated with the PDE7 enzyme. In the case of treating a particular disease or condition characterized by dysregulation of PDE7, the desired response is inhibiting the progression of the disease. This may involve only slowing the progression of the disease temporarily, although more preferably, it involves halting the progression of the disease permanently. This can be monitored by routine methods or can be monitored according to diagnostic methods of the invention discussed herein. The desired response to treatment of the disease or condition also can be delaying the onset or even preventing the onset of the disease or condition.

Such amounts will depend, of course, on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

In some embodiments, the amount of the TAA compound is sufficient to inhibit the activity of a PDE7 enzyme, such as PDE7A1 by at least 30% (e.g., by at least 50%, 60%, 70%, 80%, 90%, or 95%).

A disease or disorder associated with dysregulation of a PDE7 enzyme is a disease or disorder, in which the over-regulation or down-regulation of the PDE7 plays a role, either directly or indirectly. Such diseases or disorder include, but are not limited to, inflammatory diseases (e.g., rheumatoid arthritis, eczema, atopic dermatitis, and allergic rhinitis), autoimmune diseases, cardiovascular diseases, neurodegenerative diseases (e.g., Parkinson's disease or Alzheimer's disease), and cancers.

The subject to be treated by the methods described herein can be a human patient or a non-human mammal. In some examples, the subject is a human patient having or suspected of having a disease associated with dysregulation of PDE7, such as those described herein. In other examples, the subject is a human patient at risk for developing the disease.

Empirical considerations, such as the half-life, generally will contribute to the determination of the dosage. Frequency of administration may be determined and adjusted over the course of therapy, and is generally, but not necessarily, based on treatment and/or suppression and/or amelioration of the target disease. Alternatively, sustained continuous release formulations of the TAA compound may be appropriate. Various formulations and devices for achieving sustained release are known in the art.

In one example, dosages for an TAA compound as described herein may be determined empirically in individuals who have been given one or more administration(s) of the compound. Individuals are given incremental dosages of the TAA compound. To assess efficacy of the compound, an indicator of the target disease can be examined during the therapy following routine medical procedures.

Generally, for administration of any of the TAA compound described herein, an initial candidate dosage can be about 2 mg/kg. For the purpose of the present disclosure, a typical daily dosage might range from about any of 0.1 μg/kg to 3 μg/kg to 30 μg/kg to 300 μg/kg to 3 mg/kg, to 30 mg/kg to 100 mg/kg or more, depending on the factors mentioned above. For repeated administrations over several days or longer, depending on the condition, the treatment is sustained until a desired suppression of symptoms occurs or until sufficient therapeutic levels are achieved to inhibit the activity of a PDE7 enzyme, thereby alleviating a symptom of the disease. An exemplary dosing regimen comprises administering an initial dose of about 2 mg/kg, followed by a weekly maintenance dose of about 1 mg/kg of the compound, or followed by a maintenance dose of about 1 mg/kg every other week. However, other dosage regimens may be useful, depending on the pattern of pharmacokinetic decay that the practitioner wishes to achieve. For example, dosing from one-four times a week is contemplated. In some embodiments, dosing ranging from about 3 μg/mg to about 2 mg/kg (such as about 3 μg/mg, about 10 μg/mg, about 30 μg/mg, about 100 μg/mg, about 300 μg/mg, about 1 mg/kg, and about 2 mg/kg) may be used. In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen (including the antibody used) can vary over time.

Alternatively, any of the TAA compounds also can be used in an in vitro assay for inhibiting a PDE7 enzyme such as PDE7A1. For example, an effective amount of the TAA compound can be placed in an enzymatic reaction mixture comprising the PDE7 enzyme and a suitable substrate. The mixture can be incubated under suitable conditions for a suitable period of time to allow for occurrence of the enzymatic reaction. The activity of the PDE enzyme in the presence and absence of the TAA compound can be determined and the inhibitory efficiency of the compound can be measured via routine methods.

Kits for Use in Treating Diseases Associated with PDE7

The present disclosure also provides kits for use in inhibiting a PDE7 enzyme (e.g., PDE7A1) and for use in treating a disease or disorder associated with the PDE7 enzyme. Such kits can include one or more containers comprising one or more TAA compounds (e.g., TAA).

In some embodiments, the kit can comprise instructions for use in accordance with any of the methods described herein. The included instructions can comprise a description of administration of the one or more TAA compounds to inhibit the PDE7 enzyme and/or treating the disease associated with the enzyme according to any of the methods described herein. The kit may further comprise a description of selecting an individual suitable for treatment based on identifying whether that individual has the target disease.

The instructions relating to the use of an TAA compound generally include information as to dosage, dosing schedule, and route of administration for the intended treatment. The containers may be unit doses, bulk packages (e.g., multi-dose packages) or sub-unit doses. Instructions supplied in the kits described herein are typically written instructions on a label or package insert (e.g., a paper sheet included in the kit), but machine-readable instructions (e.g., instructions carried on a magnetic or optical storage disk) are also acceptable.

The label or package insert indicates that the composition is used for inhibiting a PDE7 enzyme and/or treating a disease associated with the enzyme may be provided for practicing any of the methods described herein.

The kits described herein are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is a TAA compound, such as TAA.

Kits may optionally provide additional components such as buffers and interpretive information. Normally, the kit comprises a container and a label or package insert(s) on or associated with the container. In some embodiments, the invention provides articles of manufacture comprising contents of the kits described above.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLE 1

Preparation of TAA-Containing Plant Extract

Leaves of shell flower (*Alpinia zerumbet*), leaves of three different strains of rice, or wheat grasses (*Triticum turanicum*) were dissolved in 1 ml HPLC eluent: 0.2 M NaH2PO4, 0.025 M TBA-HS, 15% ACN (v/v), pH6. The resultant samples were subjected to ultra-sonication for 10 minutes and then centrifuged for 10 minutes. The supernatants were filtered through a Nylon Syringe filters 0.22 um (Dia. 13 mm, STERLITECH Corporation) to produce plant extracts containing TAA.

The concentration of TAA in the plant extracts thus prepared ranges from 10-19 μg/ml. See Table 1 below:

TABLE 1

| trans-aconitic acid concentration in different plant extractions. | | | | | |
|---|---|---|---|---|---|
| Sample | Shell flower | Rice No. 11[a] | Rice No. 64 | Rice No. 67 | wheat grasses |
| Conc. (mg/ml) | 0.011 | 0.012 | 0.010 | 0.010 | 0.019 |

[a]Strain number followed from Taiwan Agricultural Research Institute.

EXAMPLE 2

TAA Specifically Inhibits PDE7

(a) PDE1 Activity and Inhibition Assay

The activity of PDE1 was determined in an enzymatic assay as described below, using:

Enzyme: 10 μg/μl PDE1 (Lot.#: SLBD8711V, SIGMA-ALDRICH)

Substrate: 0.001 M Bis-p-nitrophenyl phosphate (Lot.#: 021M5003V, SIGMA-5 ALDRICH)

Buffer: 0.1M Tris-HCl, pH 8.9

Inhibitor (trans-aconitic acid (TAA), Calycosin, Kaempferol 3-O-rutinoside, and Wogonin): 1 μg/μl (final concentration 0.125 μg/μl)

An example of the enzymatic assay is illustrated in FIG. 1. Briefly, substrate (50 μl) and buffer (200 μl) were placed in a plastic disposable cuvette (Cat.#: BL6224, Basic Life). PDE1 (100 μl) and each of the four inhibitors (50 μl) or the buffer (50 μl) as a control were then added into the cuvette. The total volume of the reaction mixture is 400 μl. After incubating the enzymatic reaction mixture for a suitable period of time, the optical density was detected by a spectrophotometer at a wave length of 405 nm (U-3300, HITACHI). The optical densities of the reaction mixtures containing the inhibitors were compared with that of the control mixture and the percentages of inhibition were calculated.

(b) PDE7 Activity and Inhibition Assay

The activity of PDE7A1 was determined in an enzymatic assay as described below, using:

Enzyme: 0.005 U/μl PDE7A1 (Cat.#: 524751, CALBIOCHEM)

Substrate: 0.0008 μg/μl cAMP (Lot.#: BCBF5219V, SIGMA-ALDRICH)

Buffer: 10 mM Tris-HCl, pH 7.5

Figure 2:
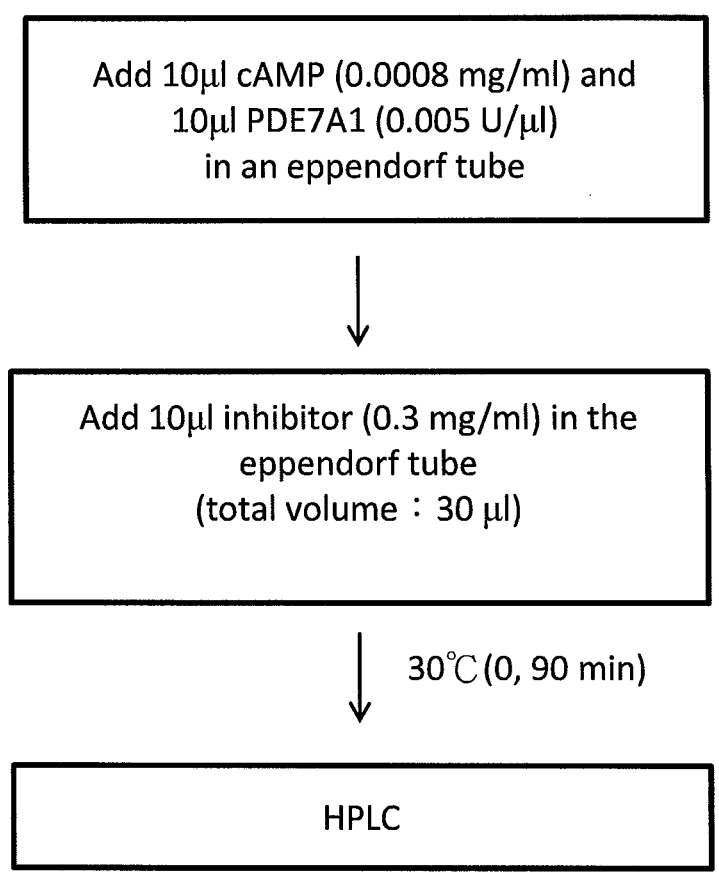
FIG. 2 is a diagram showing an assay for determining PDE7A1 enzymatic activity.

Inhibitor as mentioned above: 0.3 μg/μl as a result final concentration 0.1 μg/μl An example of the enzymatic assay for determining the activity of PDE7A1 is illustrated in FIG. 2. Briefly, substrate (10 μl), PDE7A1 (10 μl), and buffer (10 μl; as a control) were placed in an eppendorf tube in a total volume of 30 μl and immediately (at 0 minute) injected into HPLC (L-7420, HITACHI) and the contents of cAMP and AMP in the reaction mixture were detected at 254 nm under the following conditions:

Column: Kromasil, 100-5 C18.NO.3637 (25 cm×4.6 mm)

Solvent: 0.2M NaH2PO4, 25 mM TBA-HS, 15% ACN, pH6

Det: 254 nm

Injvol: 20 μl

Flow rate: 1 ml/min

The peak areas of the cAMP and AMP were measured.

90 minutes later, the control mixture was injected again into the HPLC apparatus and the peak areas of cAMP and AMP were measured as described above and compared with that of the initial injection.

Reaction mixtures containing each of the four inhibitors (10 μl) in the same total volume were injected into the HPLC apparatus following the same procedure as described above and the peak areas of cAMP and AMP were measured and compared with that of the control sample. The percentages of inhibition were calculated.

(c) Results

Figure 3:
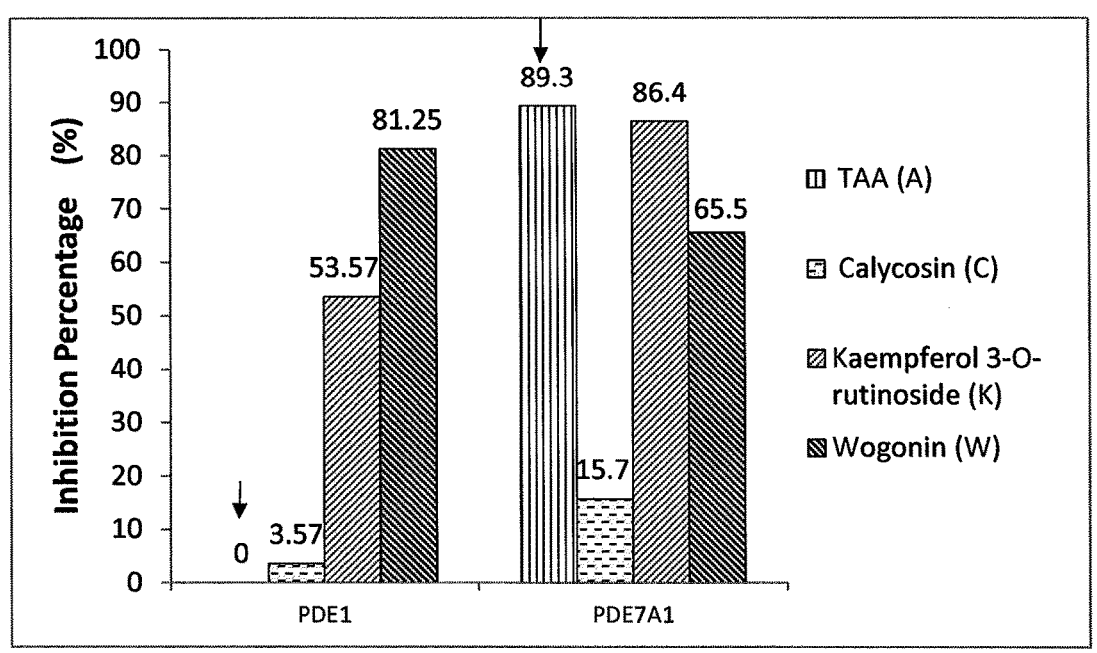
FIG. 3 is a chart showing the inhibitory activity of TAA (A), Calycosin (C), Kaempferol 3-O-rutinoside (K), and Wogonin (W) against PDE1 and PDE7A1. Arrows indicate the specific inhibition of PDE1 and PDE7A1 by trans-aconitic acid. A: trans-aconitic acid, C: Calycosin, K: Kaempferol 3-O-rutinoside, W: Wogonin.

As shown in FIG. 3, TAA specifically inhibits PDE7A1, but not PDE1. Thus, TAA, which can be purified from plant extracts, can be used in treating diseases such as inflammatory diseases and others described herein without causing side effects resulting from inhibiting PDE1.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method for treating a subject having a disease associated with dysregulation of a phosphodiesterase 7 (PDE7), comprising: administering a composition comprising trans-aconitic acid to the subject in an amount of 0.1 μg/Kg to 100 mg/Kg inhibit the activity of the PDE7 in the subject.

2. The method of claim 1, wherein the PDE7 is a human enzyme.

3. The method of claim 1, wherein the PDE7 is PDE7A1.

4. The method of claim 1, wherein the composition is a plant extract.

5. The method of claim 4, wherein the plant extract is prepared from a monocotyledon plant.

6. The method of claim 5, wherein the monocotyledon plant is shell flower, rice, wheat grass, maize, barley, or sorghum.

7. The method of claim 4, wherein the plant extract is prepared from leaves or straws of the plant.

8. The method of claim 7, wherein the plant extract is prepared from leaves or straws of rice, leaves of shell flower, or wheat grasses.

9. The method of claim 1, wherein the disease is selected from the group consisting of an inflammatory disease, an autoimmune disease, a cardiovascular disease, a neurodegenerative disease, and cancer.

10. The method of claim 9, wherein the inflammatory disease is selected from the group consisting of rheumatoid arthritis, eczema, atopic dermatitis, and allergic rhinitis.

* * * * *